United States Patent
Hsieh

(10) Patent No.: US 6,980,681 B1
(45) Date of Patent: Dec. 27, 2005

(54) METHODS AND APPARATUS FOR HELICAL RECONSTRUCTION FOR MULTISLICE CT SCAN

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/557,108

(22) Filed: Apr. 24, 2000

(51) Int. Cl.⁷ .............................................. G06K 9/00
(52) U.S. Cl. ................... 382/131; 250/363.02
(58) Field of Search ............... 282/128, 131, 282/132; 378/4

(56) References Cited

U.S. PATENT DOCUMENTS

| | | | | |
|---|---|---|---|---|
| 5,233,518 A | * | 8/1993 | King et al. | 378/14 |
| 5,513,120 A | * | 4/1996 | Berlad | 708/290 |
| 5,828,718 A | | 10/1998 | Ruth et al. | |
| 5,848,117 A | | 12/1998 | Urchuk et al. | |
| 5,946,371 A | * | 8/1999 | Lai | 378/19 |
| 5,974,108 A | * | 10/1999 | Taguchi et al. | 378/4 |
| 6,196,715 B1 | * | 3/2001 | Nambu et al. | 378/197 |
| 6,269,139 B1 | | 7/2001 | Hsieh | |
| 6,285,732 B1 | | 9/2001 | Hsieh | |
| 6,353,653 B1 | * | 3/2002 | Edic | 378/8 |

* cited by examiner

Primary Examiner—Samir Ahmed
Assistant Examiner—Charles Kim
(74) Attorney, Agent, or Firm—Carl B. Horton, Esq.; Armstrong Teasdale LLP

(57) ABSTRACT

One embodiment of the present invention is a method for imaging an object with a computed tomographic (CT) imaging system that includes steps of helically scanning the object with a multi-slice CT imaging system to acquire attenuation measurements of the object, the measurements including more than two conjugate samples for estimation of a projection at a plane of reconstruction of the object; and filtering and backprojecting the attenuation measurements of the object, including the more than two conjugate samples, to reconstruct at least one image slice of the object. An improved sampling pattern and better use of the attenuation samples obtained during a scan is thus provided.

30 Claims, 4 Drawing Sheets

METHODS AND APPARATUS FOR HELICAL RECONSTRUCTION FOR MULTISLICE CT SCAN

BACKGROUND OF THE INVENTION

This invention relates generally to methods and apparatus for computed tomographic (CT) imaging, and more specifically to methods and apparatus for acquiring and reconstructing helically scanned, medical CT images using a multi-slice CT imaging system.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. In a helical scan, a table on which the object is resting moves so that the object itself moves though the imaging plane while it is being scanned. A multi-slice CT imaging system has a plurality of parallel detector rows configured to acquire attenuation measurements corresponding to one or more two-dimensional image slices of an object. The number of image slices and the thicknesses represented by the slices is dependent upon how (and whether) attenuation measurements from the parallel detector rows are combined.

One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Helical reconstruction algorithms for multi-slice CT have been a focus for many studies. In one known CT imaging system, a reconstruction algorithm is implemented for two special helical pitches: 3:1 and 6:1. This algorithm utilizes two conjugate samples from different detector rows to estimate projection samples at a reconstruction plane using linear interpolation. Although this method performs satisfactorily in many cases, it has a number of shortcomings. First, the sampling pattern is not always optimum because only two samples on either side of the plane of reconstruction are selected. For example, samples that are closer to the reconstruction plane but located on the same side of the plane will not be utilized. Second, a 3:1 helical pitch is non-optimal for projection sampling, because the first and last detector rows measure identical ray paths, reducing the amount of non-redundant information that is acquired. In fact, in one known helical reconstruction implementation, measured projections (after calibration) of these two rows are summed first before reconstruction takes place. Third, sharp structures in the original object (along a z-axis) are suppressed and degraded slice sensitivity profiles are obtained because linear interpolation suppresses high frequency information in the sampled data.

It would therefore be desirable to provide methods and apparatus for helical reconstruction in multi-slice CT imaging systems that overcome the above-described shortcomings of known image reconstruction systems.

BRIEF SUMMARY OF THE INVENTION

There is therefore provided, in one embodiment of the present invention, a method for imaging an object with a computed tomographic (CT) imaging system that includes steps of helically scanning the object with a multi-slice CT imaging system to acquire attenuation measurements of the object, the measurements including more than two conjugate samples for estimation of a projection at a plane of reconstruction of the object; and filtering and backprojecting the attenuation measurements of the object, including the more than two conjugate samples, to reconstruct at least one image slice of the object.

This embodiment and others provide, among other advantages, an improved sampling pattern and better use of the attenuation samples obtained during a scan.

DETAILED DESCRIPTION OF THE INVENTION

Figure 1:
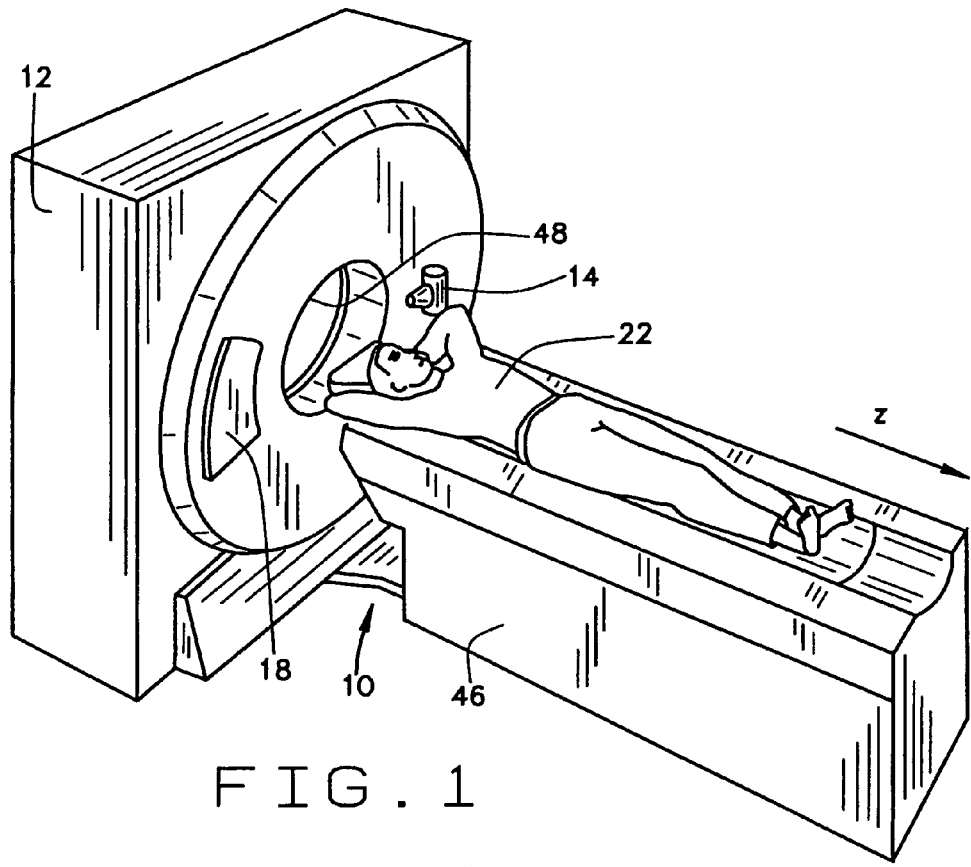
FIG. 1 is a pictorial view of a CT imaging system.
Figure 2:
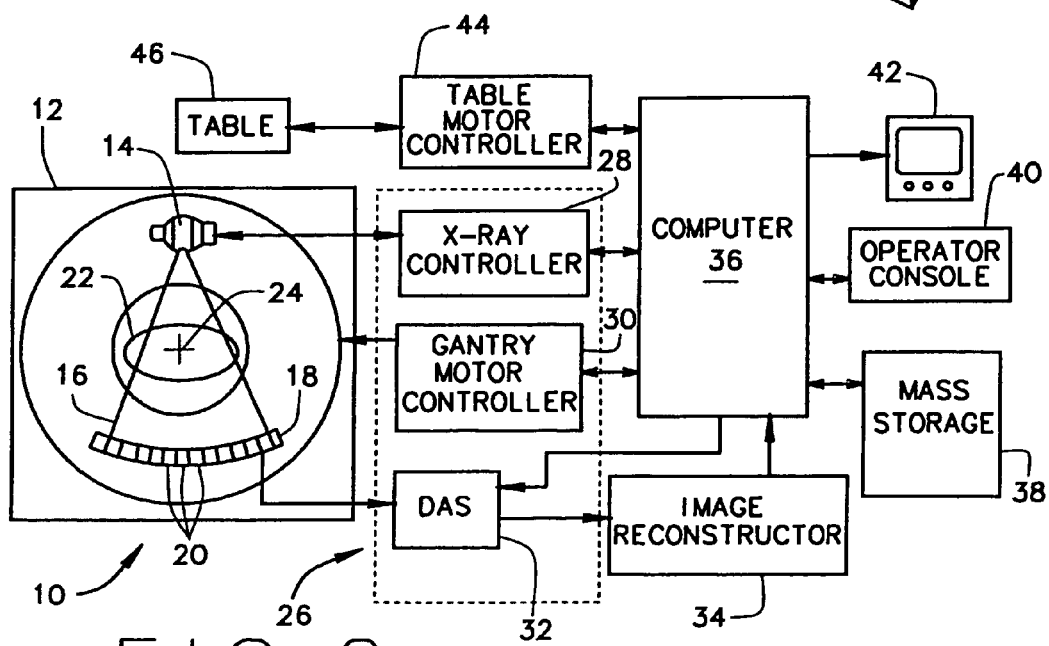
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. During a helical scan, this motion occurs while scanning is taking place.

In one embodiment of the present invention, various shortcomings of known CT image reconstruction systems are overcome by using more than two conjugate samples for estimation of a projection at a plane of reconstruction (POR). This embodiment uses as many samples as the sampling pattern supports. The samples are located within a predetermined distance from the POR. Another feature of this embodiment is that non-integer pitch helical scans are performed for pitches that are numerically less than the number of detector rows. In other words, if the number of detector rows is N, a pitch P:1 is used, where P is not an integer, and P<N. For example, a 2.5:1 pitch is used in one embodiment having four detector rows so that no duplicated samples are acquired. Yet another feature of this embodiment is the use of nonlinear interpolation techniques to preserve high frequency image components. Examples of suitable nonlinear interpolation include Lagrange interpolation and weighted interpolation-extrapolation, among others. Interpolation takes place by weighting projections prior to the filtered backprojection.

Figure 3:
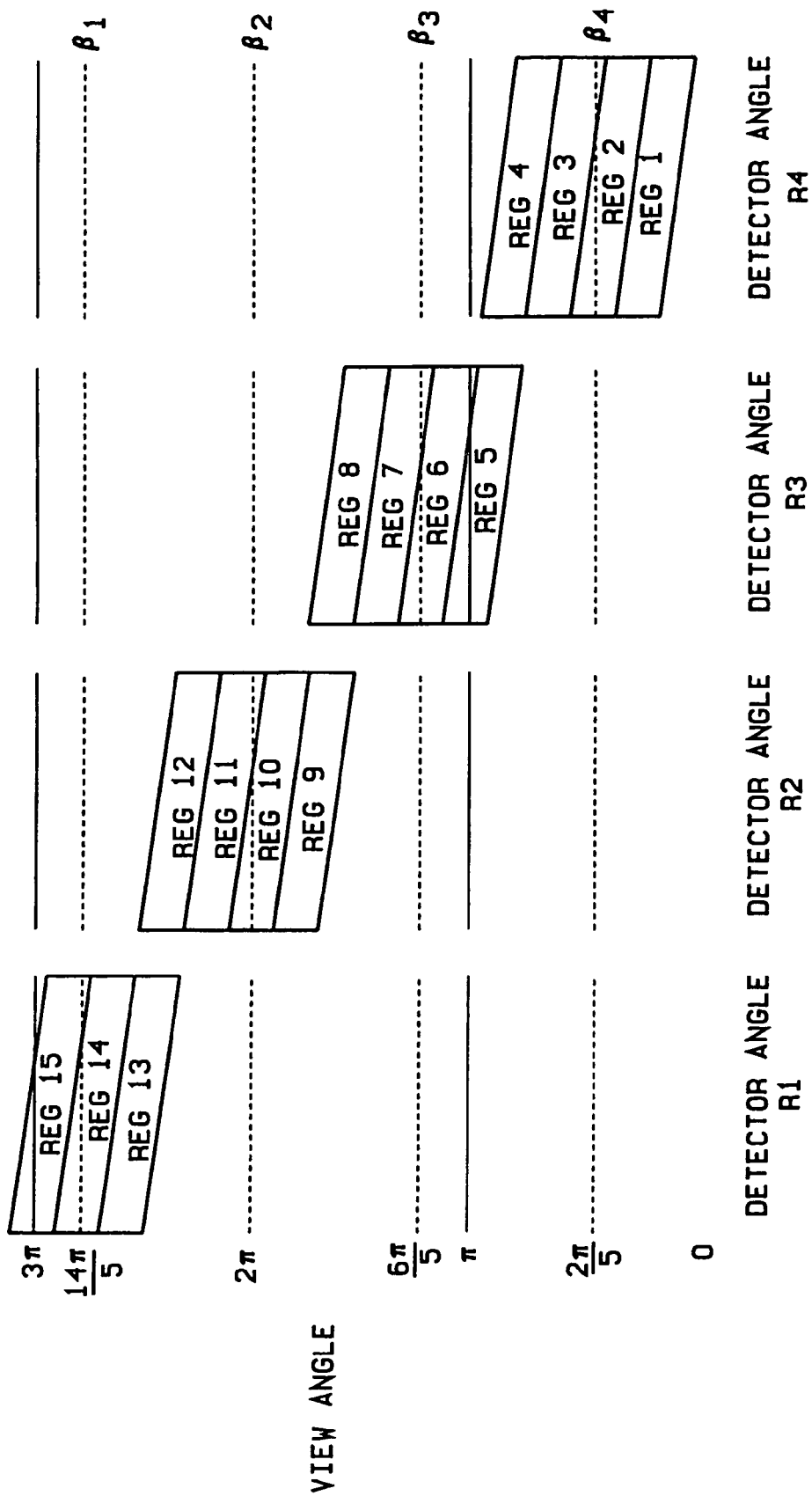
FIG. 3 is an illustration of a sampling pattern for image reconstruction in an embodiment of the invention employing a 2.5:1 helical pitch scan.

In one embodiment and referring to FIG. 3, a system 10 having four detector rows R1, R2, R3, and R4 is used with a 2.5:1 helical pitch. Sampling patterns are depicted as a function of projection view angle, detector angle, and detector row. β1, β2, β3, and β4 represent view angles at which corresponding detector rows R1, R2, R3, and R4 intersect a POR (not shown). These angles are arbitrarily selected, as only a relative angular span between them is important for any selected helical pitch. For this embodiment, an angular distance between adjacent rows that intersect the POR is 0.8π. In FIG. 3, regions REG1, REG6, and REG11 are examples of conjugate regions, because samples in these regions differ in their view angles by either π or 2π. Each projection sample at the plane of reconstruction is estimated based on conjugate samples selected from three conjugate regions.

A "region 16" that would be located above REG15 could be included, since that region would also fall within a predetermined distance from POR. However, "region 16" is excluded in this embodiment to provide improved temporal resolution. For each set of conjugated regions, three regions are included in this embodiment. If a "region 16" were included, the conjugate regions would include four regions 1, 6, 11 and 16. To provide the best temporal resolution, this embodiment seeks to formulate a smallest data set, in terms of view angle span, for image reconstruction. Including "region 16" would increase the entire angular span, as well as increase computation time and reduce uniformity.

Figure 6:
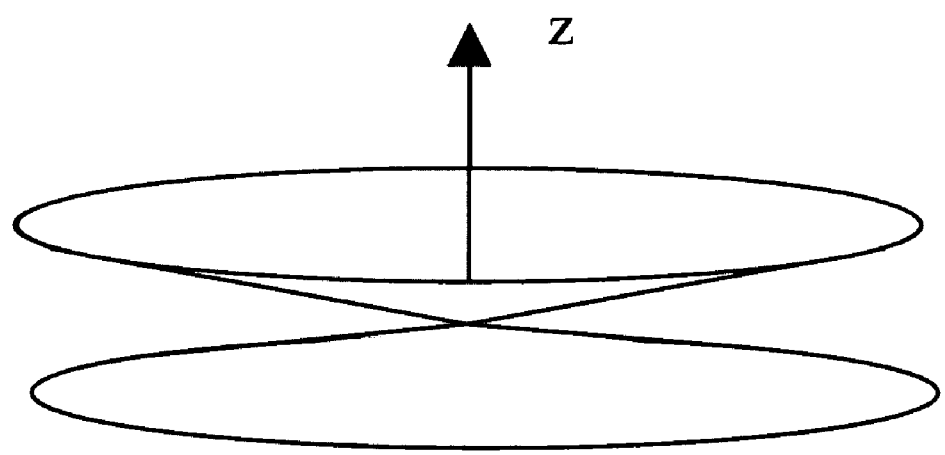
FIG. 6 is a drawing of a curved plane of reconstruction.

Weights depend upon divisions of the region. To preserve symmetry and other properties, in one embodiment, projections are estimated along a curved plane written as $\beta_1'=2.8\pi-\gamma$, $\beta_2'=2\pi-\gamma$, $\beta_3'=1.2\pi-\gamma$, and $\beta_4'=0.4\pi-\gamma$, where $\beta_1'$, $\beta_2'$, $\beta_3'$, and $\beta_4'$ represent view angles in a curved plane for corresponding detector rows R1, R2, R3, and R4, respectively. Each curved plane is defined by boundary conditions given by regions cited in equations (1) to (4). An example of a curved plane is shown in FIG. 6. In this notation, $\gamma$ represents the detector angle. Weights for third-order Lagrange interpolation for rows R1, R2, R3, and R4, respectively, are written as:

$$w_1(\gamma, \beta) = \begin{cases} \frac{25}{6\pi^2}\left(\beta - \beta_1' + \frac{2\pi}{5}\right)\left(\beta - \beta_1' + \frac{3\pi}{5}\right) & \beta_1' - \frac{2\pi}{5} \le \beta < \beta_1' - \frac{\pi}{5} \\ -\frac{25}{2\pi^2}\left(\beta - \beta_1' + \frac{2\pi}{5}\right)(\beta - \beta_1' - \frac{\pi}{5}) & \beta_1' - \frac{\pi}{5} \le \beta < \beta_1' \\ \frac{25}{2\pi^2}\left(\beta - \beta_1' - \frac{2\pi}{5}\right)\left(\beta - \beta_1' + \frac{\pi}{5}\right) & \beta_1' \le \beta < \beta_1' + \frac{\pi}{5} \end{cases} \quad (1)$$

$$w_2(\gamma, \beta) = \begin{cases} \frac{25}{3\pi^2}\left(\beta - \beta_2' + \frac{3\pi}{5}\right)(\beta - \beta_2' + \frac{\pi}{5}) & \beta_2' - \frac{2\pi}{5} \le \beta < \beta_2' - \frac{\pi}{5} \\ -\frac{25}{2\pi^2}(\beta - \beta_2' - \frac{\pi}{5})(\beta - \beta_2' + \frac{\pi}{5}) & \beta_2' - \frac{\pi}{5} \le \beta < \beta_2' \\ \frac{25}{2\pi^2}\left(\beta - \beta_2' - \frac{2\pi}{5}\right)(\beta - \beta_2' - \frac{\pi}{5}) & \beta_2' \le \beta < \beta_2' + \frac{2\pi}{5} \end{cases} \quad (2)$$

$$w_3(\gamma, \beta) = \begin{cases} \frac{25}{2\pi^2}(\beta - \beta_3' + \frac{\pi}{5})\left(\beta - \beta_3' + \frac{2\pi}{5}\right) & \beta_3' - \frac{2\pi}{5} \le \beta < \beta_3' - \frac{\pi}{5} \\ -\frac{25}{\pi^2}(\beta - \beta_3' - \frac{\pi}{5})(\beta - \beta_3' + \frac{\pi}{5}) & \beta_3' - \frac{\pi}{5} \le \beta < \beta_3' + \frac{\pi}{5} \\ \frac{25}{3\pi^2}(\beta - \beta_3' - \frac{\pi}{5})\left(\beta - \beta_3' - \frac{3\pi}{5}\right) & \beta_3' + \frac{\pi}{5} \le \beta < \beta_3' + \frac{2\pi}{5} \end{cases} \quad (3)$$

$$w_4(\gamma, \beta) = \begin{cases} \frac{25}{2\pi^2}(\beta - \beta_4' + \frac{\pi}{5})\left(\beta - \beta_4' + \frac{2\pi}{5}\right) & \beta_4' - \frac{2\pi}{5} \le \beta < \beta_4' \\ -\frac{25}{2\pi^2}(\beta - \beta_4' + \frac{\pi}{5})\left(\beta - \beta_4' - \frac{2\pi}{5}\right) & \beta_4' \le \beta < \beta_4' + \frac{\pi}{5} \\ \frac{25}{6\pi^2}\left(\beta - \beta_4' - \frac{3\pi}{5}\right)\left(\beta - \beta_4' - \frac{2\pi}{5}\right) & \beta_4' + \frac{\pi}{5} \le \beta < \beta_4' + \frac{2\pi}{5} \end{cases} \quad (4)$$

Figure 4:
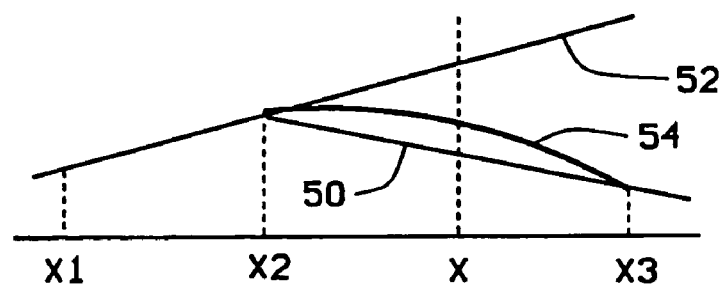
FIG. 4 is an illustration of interpolation, extrapolation, and weighted interpolation-extrapolation techniques to estimate an attenuation value at a point x.

In one embodiment of the present invention, weighted interpolation-extrapolation (WIE), i.e., a combining of weighted interpolation measurements with weighted extrapolated measurements, is used prior to the filtered backprojection. FIG. 4 illustrates an example having three sampling points that are located on both sides of a point x where the interpolation is to take place. (A different case in which one sample is located at left and two samples at the right is treated similarly.) For one known helical reconstruction algorithm, only x2 and x3 are used for linear interpolation represented by line 50. Weights t2 and t3 used for x2 and x3, respectively, are written as:

$$t2 = \frac{x3 - x}{x3 - x2} \quad (5)$$

$$t3 = \frac{x - x2}{x3 - x2}$$

In one embodiment of the present invention, to use points x1 and x2 to estimate x, extrapolation is used as represented by line 52. Weights for x1 and x2 (denoted by e1 and e2) are written as:

$$e1 = \frac{x2 - x}{x2 - x1} \quad (6)$$

$$e2 = \frac{x - x1}{x2 - x1}$$

In this notation, x1, x2, and x3 are x-axis coordinates of locations of measured signals, and x is the location of the signal to be estimated. The weights used in linear interpolation are calculated based on a relative distance of the two points to the interpolation location. Combined weights for points x1, x2, and x3 (denoted by q1, q2, and q3, respectively) are written as:

$$q1 = (1 - t_2^\alpha - t_3^\alpha) e1,$$

$$q2 = (1 - t_2^\alpha - t_3^\alpha) e2 + (t_2^\alpha + t_3^\alpha) t2,$$

$$q3 = (t_2^\alpha + t_3^\alpha) t3. \quad (7)$$

In equation (7), $\alpha$ is a parameter that adjusts relative strength and contributions of the extrapolation. The terms q1, q2, and q3 represent weights for the three measured samples to estimate a sample in the POR.

This interpolation scheme overcomes the shortcomings of linear interpolation and enables a better preservation of high frequency information contents. Weighting functions for rows R1, R2, R3, and R4, respectively, for this interpolation scheme, represented by line 54, are written as:

$$w_1(\gamma, \beta) = \quad (8)$$

$$\begin{cases} \left[\left(\frac{5\theta_1 + 2\pi}{2\pi}\right)^\alpha + \left(\frac{-5\theta_1}{2\pi}\right)^\alpha\right]\left(\frac{5\theta_1 + 2\pi}{2\pi}\right), & \beta_1' - \frac{2\pi}{5} \leq \beta < \beta_1' - \frac{\pi}{5} \\ \left[1 - \left(\frac{5\theta_1 + 2\pi}{2\pi}\right)^\alpha - \left(\frac{-5\theta_1}{2\pi}\right)^\alpha\right]\left(\frac{\pi - 5\theta_1}{\pi}\right) + \\ \left[\left(\frac{5\theta_1 + 2\pi}{2\pi}\right)^\alpha + \left(\frac{-5\theta_1}{2\pi}\right)^\alpha\right]\left(\frac{5\theta_1 + 2\pi}{2\pi}\right), & \beta_1' - \frac{\pi}{5} \leq \beta < \beta_1' \\ \left[\left(\frac{5\theta_1}{\pi}\right)^\alpha + \left(\frac{\pi - 5\theta_1}{\pi}\right)^\alpha\right]\left(\frac{\pi - 5\theta_1}{\pi}\right), & \beta_1' \leq \beta < \beta_1' + \frac{\pi}{5} \end{cases}$$

where $\theta_1 = \beta - \beta_1' = \beta - 2.8\pi + \gamma$, $$w_2(\gamma, \beta) = \quad (9)$$

$$\begin{cases} \left[1 - \left(\frac{5\theta_2 + 3\pi}{2\pi}\right)^\alpha - \left(\frac{-5\theta_2 - \pi}{2\pi}\right)^\alpha\right]\left(\frac{5\theta_2 + \pi}{\pi}\right), & \beta_2' - \frac{2\pi}{5} \leq \beta < \beta_2' - \frac{\pi}{5} \\ \left[1 - \left(\frac{5\theta_2 + \pi}{\pi}\right)^\alpha - \left(\frac{-5\theta_2}{\pi}\right)^\alpha\right]\left(\frac{\pi - 5\theta_2}{\pi}\right) + \\ \left[\left(\frac{5\theta_2 + \pi}{\pi}\right)^\alpha + \left(\frac{-5\theta_2}{\pi}\right)^\alpha\right]\left(\frac{5\theta_2 + \pi}{\pi}\right), & \beta_2' - \frac{\pi}{5} \leq \beta < \beta_2' \\ \left[\left(\frac{5\theta_2}{\pi}\right)^\alpha + \left(\frac{\pi - 5\theta_2}{\pi}\right)^\alpha\right]\left(\frac{\pi - 5\theta_2}{\pi}\right), & \beta_2' \leq \beta < \beta_2' + \frac{\pi}{5} \\ \left[1 - \left(\frac{5\theta_2 - \pi}{\pi}\right)^\alpha - \left(\frac{2\pi - 5\theta_2}{\pi}\right)^\alpha\right]\left(\frac{\pi - 5\theta_2}{\pi}\right), & \beta_2' + \frac{\pi}{5} \leq \beta < \beta_2' + \frac{2\pi}{5} \end{cases}$$

where $\theta_2 = \beta - \beta_2' = \beta - 2\pi + \gamma$, $$w_3(\gamma, \beta) = \quad (10)$$

$$\begin{cases} \left[1 - \left(\frac{5\theta_3 + 2\pi}{\pi}\right)^\alpha - \\ \left(\frac{-5\theta_3 - \pi}{\pi}\right)^\alpha\right]\left(\frac{5\theta_3 + \pi}{\pi}\right), & \beta_3' - \frac{2\pi}{5} \leq \beta < \beta_3' - \frac{\pi}{5} \\ \left[1 - \left(\frac{5\theta_3 + \pi}{\pi}\right)^\alpha - \left(\frac{-5\theta_3}{\pi}\right)^\alpha\right]\left(\frac{\pi - 5\theta_3}{\pi}\right) + \\ \left[\left(\frac{5\theta_3 + \pi}{\pi}\right)^\alpha + \left(\frac{-5\theta_3}{\pi}\right)^\alpha\right]\left(\frac{5\theta_3 + \pi}{\pi}\right), & \beta_3' - \frac{\pi}{5} \leq \beta < \beta_3' \\ \left[1 - \left(\frac{5\theta_3}{\pi}\right)^\alpha - \left(\frac{\pi - 5\theta_3}{\pi}\right)^\alpha\right]\left(\frac{\pi + 5\theta_3}{\pi}\right) + \\ \left[\left(\frac{5\theta_3}{\pi}\right)^\alpha + \left(\frac{\pi - 5\theta_3}{\pi}\right)^\alpha\right]\left(\frac{\pi - 5\theta_3}{\pi}\right), & \beta_3' \leq \beta < \beta_3' + \frac{\pi}{5} \\ \left[1 - \left(\frac{5\theta_3 - \pi}{2\pi}\right)^\alpha - \\ \left(\frac{3\pi - 5\theta_3}{2\pi}\right)^\alpha\right]\left(\frac{\pi - 5\theta_3}{\pi}\right), & \beta_3' + \frac{\pi}{5} \leq \beta < \beta_3' + \frac{2\pi}{5} \end{cases}$$

where $\theta_3 = \beta - \beta_3' = \beta - 1.2\pi + \gamma$, and $$w_4(\gamma, \beta) = \quad (11)$$

$$\begin{cases} \left[1 - \left(\frac{5\theta_4 + 2\pi}{\pi}\right)^\alpha - \\ \left(\frac{-5\theta_4 - \pi}{\pi}\right)^\alpha\right]\left(\frac{5\theta_4 + \pi}{\pi}\right), & \beta_4' - \frac{2\pi}{5} \leq \beta < \beta_4' - \frac{\pi}{5} \\ \left[\left(\frac{5\theta_4 + \pi}{\pi}\right)^\alpha + \left(\frac{-5\theta_4}{\pi}\right)^\alpha\right]\left(\frac{\pi + 5\theta_4}{\pi}\right), & \beta_4' - \frac{\pi}{5} \leq \beta < \beta_4' \\ \left[1 - \left(\frac{5\theta_4}{2\pi}\right)^\alpha - \left(\frac{2\pi - 5\theta_4}{2\pi}\right)^\alpha\right]\left(\frac{\pi + 5\theta_4}{\pi}\right) + \\ \left[\left(\frac{5\theta_4}{2\pi}\right)^\alpha + \left(\frac{2\pi - 5\theta_4}{2\pi}\right)^\alpha\right]\left(\frac{2\pi - 5\theta_4}{2\pi}\right), & \beta_4' \leq \beta < \beta_4' + \frac{\pi}{5} \\ \left[\left(\frac{5\theta_4}{2\pi}\right)^\alpha + \\ \left(\frac{2\pi - 5\theta_4}{2\pi}\right)^\alpha\right]\left(\frac{2\pi - 5\theta_4}{2\pi}\right), & \beta_4' + \frac{\pi}{5} \leq \beta < \beta_4' + \frac{2\pi}{5} \end{cases}$$

where $\theta_4 = \beta - \beta_4' = \beta - 0.4\pi + \gamma$,

In equations (8)–(11), w1, w2, w3, and w4 are derived weights for four rows, based on conjugate regions shown in FIG. 3 and in equation (7). For each sample to be estimated on POR, three conjugate samples are selected, based on FIG. 3, and equation (7) is applied to determine their weights. The three conjugate samples could, for example, come from any three of R1, R2, R3, and R4.

Figure 5:
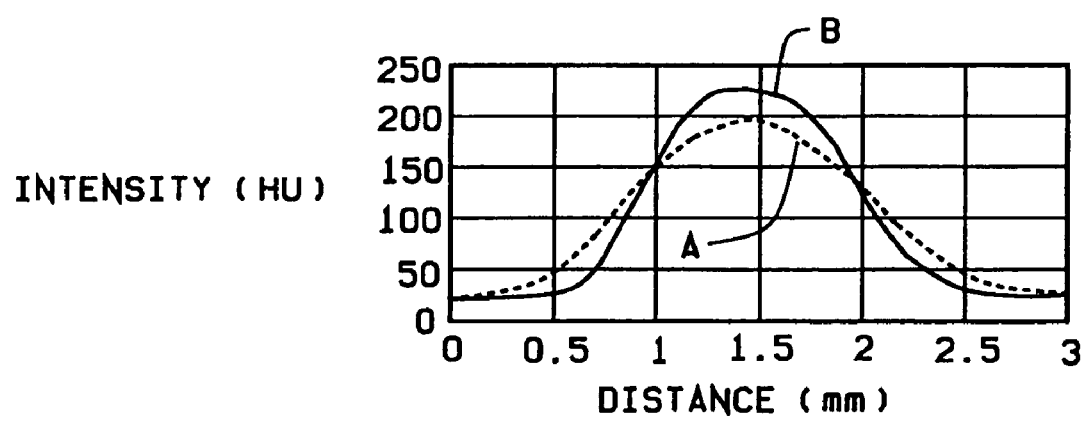
FIG. 5 is a graph of slice sensitivity profile measurements using a thin slice phantom, comparing a slice profile using a known technique utilizing a 3:1 helical pitch scan to an embodiment of the present invention utilizing a 2.5:1 helical pitch scan.

To demonstrate the advantages of the use of the above reconstruction weights expressed in equations (8)–(11), a phantom study was performed. In this study, a thin plate placed parallel to an x-y plane inside a 20 cm poly phantom was scanned with 120 kV/200 mA/1.25 mm/1.25 sec at both 3:1 and 2.5:1 pitches. Images were reconstructed every 0.1 mm to ensure adequate samples to map out slice profiles. For the 3:1 helical pitch, a known reconstruction algorithm was used. For the 2.5:1 helical pitch, the weights expressed in equations (8)–(11) were used. Profiles of the thin plates (and therefore, a system slice sensitivity profile) were calculated for both cases. To avoid effects of statistical noise due to finite x-ray photon statistics, each point on a profile curve is an average over a 21 by 21 pixel region (in an x-y plane) centered on the thin plate. FIG. 5 depicts a slice profile A for a 3:1 helical pitch image reconstructed using the known reconstruction algorithm and a slice profile B for a 2.5:1 helical pitch image reconstructed using the weight functions expressed in equations (8)–(11). A much narrower slice profile is obtained and the peak intensity for the profile is higher when equations (8)–(11) are used.

To more fully evaluate a WIE reconstruction embodiment of the present invention, a noise analysis was performed. For comparison, images in z of WIE were smoothed by a filter kernel such that WIE with smoothing provides the same slice profile as the known algorithm without smoothing. A kernel that satisfies this condition has been found to be an 11-point kernel with coefficients [0.5, 1, 1, ..., 1, 1, 0.5].

Image smoothing (in z) for the WIE images was also performed for a case in which the phantom was uniform in z. The standard deviation of the smoothed image was determined to be 5.23 HU. The standard deviation observed using the known algorithm was 6.63 HU. This result indicates that for the same slice sensitivity profile, a nearly 37% mA reduction can be achieved, if the noise is to be maintained at the same level. In images corresponding to the location where the thin plate is located, WIE-weighted images with smoothing show less image artifacts than images reconstructed using the known reconstruction algorithm.

In another embodiment, an equivalent result to a non-linear interpolation is achieved by multiplying a set of projection date by a set of weights. The weights, for a third order Lagrange interpolation, are written as equations (1)–(4), while weights for WEE are written as equations (8)–(11).

It will thus be seen that embodiments of the present invention provide better sampling patterns, acquire less redundant information, result in less suppression of sharp structures of object and better slice sensitivity profiles than known helical CT image reconstruction methods and systems.

Although the exemplary embodiments described herein and having test results presented herein are 4-slice embodiments, other embodiments of the invention are applicable to multi-slice CT imaging systems providing different numbers of image slices. For example, in other embodiments, 8-slice, 16-slice, 32-slice, etc. CT imaging systems are used. In addition, the invention is not limited to embodiments providing a 2.5:1 helical pitch. This pitch was selected for purposes of illustration only. Other embodiments of the invention are applicable to CT imaging systems providing different helical pitches. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam.

While the invention has been described in terms of various specific embodiments, those skilled in the art will recognize that the invention can be practiced with modification within the spirit and scope of the claims. Accordingly, the spirit and scope of the invention are to be limited only by the terms of the appended claims.

What is claimed is:

1. A method for imaging an object with a computed tomographic (CT) imaging system, comprising the steps of:
   helically scanning the object with a multi-slice CT imaging system having a plurality of detector rows to acquire attenuation measurements of the object, the measurements including more than two conjugate samples, wherein a difference between a view angle of one of the more than two conjugate samples and a view angle of any one of the remaining conjugate samples of the more than two conjugate samples is n π, wherein n is an integer greater than zero;
   estimating at least one projection along a curved plane of reconstruction of the object using the attenuation measurements of the object, including the more than two conjugate samples;
   applying different weighting functions within each detector row dependent upon a division of conjugate regions for each detector row and dependent upon view angles in a curved plane for corresponding detector rows; and
   filtering and backprojecting the attenuation measurements of the object, including the more than two conjugate samples, to reconstruct at least one image slice of the object.

2. A method in accordance with claim 1 wherein the more than two conjugate samples are located within a predetermined distance from the curved plane of reconstruction of the object.

3. A method in accordance with claim 1 wherein the CT imaging system has N detector rows, and further comprising the step of selecting a helical pitch P:1 for said helical scan, where P is a non-integer less than N.

4. A method in accordance with claim 3 wherein N=4 and P=2.5.

5. A method in accordance with claim 1 further comprising the step of applying a non-linear interpolation to the attenuation measurements prior to said filtering and backprojecting.

6. A method in accordance with claim 5 wherein applying a non-linear interpolation to the attenuation measurements comprises applying a Lagrange interpolation to the attenuation measurements.

7. A method in accordance with claim 6 wherein applying a Lagrange interpolation to the attenuation measurements comprises applying third order Lagrange interpolation weights to measurements from four detector rows.

8. A method in accordance with claim 5 wherein the CT imaging system has 4 detector rows, helically scanning the object to obtain attenuation measurements comprises the step of helically scanning the object at a pitch of 2.5:1, and said estimating at least one projection along the curved plane of reconstruction comprises the step of estimating projections along the curved plane of reconstruction written as $\beta_1'=2.8\pi-\gamma$, $\beta_2'=2\pi-\gamma$, $\beta_3'=1.2\pi-\gamma$, and $\beta_4'=0.4\pi-\gamma$, where $\beta_1'$, $\beta_2'$, $\beta_3'$, and $\beta_4'$ represent view angles in a curved plane for corresponding detector rows R1, R2, R3, and R4, respectively, and $\gamma$ represents a detector angle.

9. A method in accordance with claim 5 wherein applying a non-linear interpolation to the attenuation measurements comprises combining weighted interpolated measurements with weighted extrapolated measurements.

10. A method in accordance with claim 9 wherein the CT imaging system has 4 detector rows R1, R2, R3, and R4, helically scanning the object to obtain attenuation measurements comprises the step of helically scanning the object at a pitch of 2.5:1, and said method further comprises the step of applying weights to attenuation measurements for detector rows R1, R2, R3, and R4 respectively, wherein the applied weights are written as:

$$w_1(\gamma, \beta) = \begin{cases} \left[\left(\frac{5\theta_1+2\pi}{2\pi}\right)^\alpha + \left(\frac{-5\theta_1}{2\pi}\right)^\alpha\right]\left(\frac{5\theta_1+2\pi}{2\pi}\right), & \beta_1' - \frac{2\pi}{5} \le \beta < \beta_1' - \frac{\pi}{5} \\ \left[1 - \left(\frac{5\theta_1+2\pi}{2\pi}\right)^\alpha - \left(\frac{-5\theta_1}{2\pi}\right)^\alpha\right]\left(\frac{\pi-5\theta_1}{\pi}\right) + \\ \left[\left(\frac{5\theta_1+2\pi}{2\pi}\right)^\alpha + \left(\frac{-5\theta_1}{2\pi}\right)^\alpha\right]\left(\frac{5\theta_1+2\pi}{2\pi}\right), & \beta_1' - \frac{\pi}{5} \le \beta < \beta_1' \\ \left[\left(\frac{5\theta_1}{\pi}\right)^\alpha + \left(\frac{\pi-5\theta_1}{\pi}\right)^\alpha\right]\left(\frac{\pi-5\theta_1}{\pi}\right), & \beta_1' \le \beta < \beta_1' + \frac{\pi}{5} \end{cases}$$

where $\theta_1 = \beta - \beta_1' = \beta - 2.8\pi + \gamma$, $$w_2(\gamma, \beta) = \begin{cases} \left[1 - \left(\frac{5\theta_2+3\pi}{2\pi}\right)^\alpha - \left(\frac{-5\theta_2-\pi}{2\pi}\right)^\alpha\right]\left(\frac{5\theta_2+\pi}{\pi}\right), & \beta_2' - \frac{2\pi}{5} \le \beta < \beta_2' - \frac{\pi}{5} \\ \left[1 - \left(\frac{5\theta_2+\pi}{\pi}\right)^\alpha - \left(\frac{-5\theta_2}{\pi}\right)^\alpha\right]\left(\frac{\pi-5\theta_2}{\pi}\right) + \\ \left[\left(\frac{5\theta_2+\pi}{\pi}\right)^\alpha + \left(\frac{-5\theta_2}{2\pi}\right)^\alpha\right]\left(\frac{5\theta_2+\pi}{\pi}\right), & \beta_2' - \frac{\pi}{5} \le \beta < \beta_2' \\ \left[\left(\frac{5\theta_2}{\pi}\right)^\alpha + \left(\frac{\pi-5\theta_2}{\pi}\right)^\alpha\right]\left(\frac{\pi-5\theta_2}{\pi}\right), & \beta_2' \le \beta < \beta_2' + \frac{\pi}{5} \\ \left[1 - \left(\frac{5\theta_2-\pi}{\pi}\right)^\alpha - \left(\frac{2\pi-5\theta_2}{\pi}\right)^\alpha\right]\left(\frac{\pi-5\theta_2}{\pi}\right), & \beta_2' + \frac{\pi}{5} \le \beta < \beta_2' + \frac{2\pi}{5} \end{cases}$$

where $\theta_2 = \beta - \beta_2' = \beta - 2\pi + \gamma$, $$w_3(\gamma, \beta) = \begin{cases} \left[1 - \left(\frac{5\theta_3+2\pi}{\pi}\right)^\alpha - \right. \\ \left.\left(\frac{-5\theta_3-\pi}{\pi}\right)^\alpha\right]\left(\frac{5\theta_3+\pi}{\pi}\right), & \beta_3' - \frac{2\pi}{5} \le \beta < \beta_3' - \frac{\pi}{5} \\ \left[1 - \left(\frac{5\theta_3+\pi}{\pi}\right)^\alpha - \left(\frac{-5\theta_3}{\pi}\right)^\alpha\right]\left(\frac{\pi-5\theta_3}{\pi}\right) + \\ \left[\left(\frac{5\theta_3+\pi}{\pi}\right)^\alpha + \left(\frac{-5\theta_3}{\pi}\right)^\alpha\right]\left(\frac{5\theta_3+\pi}{\pi}\right), & \beta_3' - \frac{\pi}{5} \le \beta < \beta_3' \\ \left[1 - \left(\frac{5\theta_3}{\pi}\right)^\alpha - \left(\frac{\pi-5\theta_3}{\pi}\right)^\alpha\right]\left(\frac{\pi+5\theta_3}{\pi}\right) + \\ \left[\left(\frac{5\theta_3}{\pi}\right)^\alpha + \left(\frac{\pi-5\theta_3}{\pi}\right)^\alpha\right]\left(\frac{\pi-5\theta_3}{\pi}\right), & \beta_3' \le \beta < \beta_3' + \frac{\pi}{5} \\ \left[1 - \left(\frac{5\theta_3-\pi}{2\pi}\right)^\alpha - \right. \\ \left.\left(\frac{3\pi-5\theta_3}{2\pi}\right)^\alpha\right]\left(\frac{\pi-5\theta_3}{\pi}\right), & \beta_3' + \frac{\pi}{5} \le \beta < \beta_3' + \frac{2\pi}{5} \end{cases}$$

where $\theta_3 = \beta - \beta_3' = \beta - 1.2\pi + \gamma$, and $$w_4(\gamma, \beta) = \begin{cases} \left[1 - \left(\frac{5\theta_4+2\pi}{\pi}\right)^\alpha - \right. \\ \left.\left(\frac{-5\theta_4-\pi}{\pi}\right)^\alpha\right]\left(\frac{5\theta_4+\pi}{\pi}\right), & \beta_4' - \frac{2\pi}{5} \le \beta < \beta_4' - \frac{\pi}{5} \\ \left[\left(\frac{5\theta_4+\pi}{\pi}\right)^\alpha + \left(\frac{-5\theta_4}{\pi}\right)^\alpha\right]\left(\frac{\pi+5\theta_4}{\pi}\right), & \beta_4' - \frac{\pi}{5} \le \beta < \beta_4' \\ \left[1 - \left(\frac{5\theta_4}{2\pi}\right)^\alpha - \left(\frac{2\pi-5\theta_4}{2\pi}\right)^\alpha\right]\left(\frac{\pi+5\theta_4}{\pi}\right) + \\ \left[\left(\frac{5\theta_4}{2\pi}\right)^\alpha + \left(\frac{2\pi-5\theta_4}{2\pi}\right)^\alpha\right]\left(\frac{2\pi-5\theta_4}{2\pi}\right), & \beta_4' \le \beta < \beta_4' + \frac{\pi}{5} \\ \left[\left(\frac{5\theta_4}{2\pi}\right)^\alpha + \right. \\ \left.\left(\frac{2\pi-5\theta_4}{2\pi}\right)^\alpha\right]\left(\frac{2\pi-5\theta_4}{2\pi}\right), & \beta_4' + \frac{\pi}{5} \le \beta < \beta_4' + \frac{2\pi}{5} \end{cases}$$

where $\theta_4 = \beta - \beta_4' = \beta - 0.4\pi + \gamma$, $\beta_1' = 2.8\pi - \gamma$, $\beta_2' = 2\pi - \gamma$, $\beta_3' = 1.2\pi - \gamma$, and $\beta_4' = 0.4\pi - \gamma$;

$\beta_1' \beta_2' \beta_3'$, and $\beta_4'$ represent view angles intersecting the POR for detector rows R1, R2, R3, and R4, respectively, and $\gamma$ represents a detector angle.

11. A method in accordance with claim 1 further comprising the step of applying a set of weights to the attenuation measurements prior to said filtering and backprojecting.

12. A method in accordance with claim 11 wherein applying a set of weights to the attenuation measurements comprises the step of applying Lagrange weights to the attenuation measurements.

13. A method in accordance with claim 12 wherein applying Lagrange weights to the attenuation measurements comprises applying third order Lagrange weights to measurements from four detector rows.

14. A method in accordance with claim 11 wherein the CT imaging system has 4 detector rows, helically scanning the object to obtain attenuation measurements comprises the step of helically scanning the object at a pitch of 2.5:1, and said estimating at least one projection along the curved plane of reconstruction comprises the step of estimating projections along the curved plane of reconstruction written as $\beta_1' = 2.8\pi - \gamma$, $\beta_2' = 2\pi - \gamma$, $\beta_3' = 1.2\pi - \gamma$, and $\beta_4' = 0.4\pi - \gamma$, where $\beta_1'$, $\beta_2'$, $\beta_3'$, and $\beta_4'$ represent view angles in a curved plane for corresponding detector rows R1, R2, R3, and R4, respectively, and $\gamma$ represents a detector angle.

15. A method in accordance with claim 1 further comprising the step of applying interpolation and extrapolation to determine weights to be applied to the attenuation measurements.

16. A computed tomographic (CT) imaging system for imaging an object, said system comprising a radiation source and a multi-slice detector having a plurality of detector rows, said multi-slice detector configured to acquire attenuation measurements of an object between said radiation source and said multi-slice detector, said system configured to:

helical scan the object to acquire attenuation measurements of the object, said measurements including more than two conjugate samples, wherein a difference between a view angle of one of the more than two conjugate samples and a view angle of any one of the remaining conjugate samples of the more than two conjugate samples is n π, wherein n is an integer greater than zero;

estimate at least one projection along a curved plane of reconstruction of the object using the attenuation measurements of the object, including the more than two conjugate samples;

applying different weighting functions within each detector row dependent upon a division of conjugate regions for each detector row and dependent upon view angles in a curved plane for corresponding detector rows: and filter and backproject the attenuation measurements of the object, including the more than two conjugate samples, to reconstruct at least one image slice of the object.

17. A system in accordance with claim 16 further configured so that the more than two conjugate samples are located within a predetermined distance from the curved plane of reconstruction of the object.

18. A system in accordance with claim 17 having N detector rows, and further configured to perform the helical scan at a pitch P:1, where P is a non-integer less than N.

19. A system in accordance with claim 18 wherein N=4 and P=2.5.

20. A system in accordance with claim 16 further configured to apply a non-linear interpolation to the attenuation measurements prior to said filtering and backprojecting.

21. A system in accordance with claim 20 wherein said system being configured to apply a non-linear interpolation to the attenuation measurements comprises said system being configured to apply a Lagrange interpolation to the attenuation measurements.

22. A system in accordance with claim 21 wherein said system being configured to apply a Lagrange interpolation to the attenuation measurements comprises said system being configured to apply third order Lagrange interpolation weights to measurements from four detector rows.

23. A system in accordance with claim 20 having 4 detector rows, and wherein said system being configured to helically scan the object to obtain attenuation measurements comprises said system being configured to helically scan the object at a pitch of 2.5:1, and to estimate at least one projection along the curved plane of reconstruction said system is further configured to estimate projections along the curved plane of reconstruction written as $\beta_1'=2.8\pi-\gamma$, $\beta_2'=2\pi-\gamma$, $\beta_3'=1.2\pi-\gamma$, and $\beta_4'=0.4\pi-\gamma$, where $\beta_1'$, $\beta_2'$, $\beta_3'$, and $\beta_4'$ represent view angles in a curved plane for corresponding detector rows R1, R2, R3, and R4, respectively, and $\gamma$ represents a detector angle.

24. A system in accordance with claim 20 wherein said system being configured to apply a non-linear interpolation to the attenuation measurements comprises said system being configured to combine weighted interpolated measurements with weighted extrapolated measurements.

25. A system in accordance with claim 24 having 4 detector rows R1, R2, R3, and R4, wherein said system being configured to helically scan the object to obtain attenuation measurements comprises said system being configured to helically scan the object at a pitch of 2.5:1, and said system is further configured to apply weights to attenuation measurements for detector rows R1, R2, R3, and R4 respectively, wherein the applied weights are written as:

$w_1(\gamma, \beta) =$ $$\begin{cases} \left[\left(\frac{5\theta_1+2\pi}{2\pi}\right)^{\alpha} + \left(\frac{-5\theta_1}{2\pi}\right)^{\alpha}\right]\left(\frac{5\theta_1+2\pi}{2\pi}\right), & \beta_1' - \frac{2\pi}{5} \leq \beta < \beta_1' - \frac{\pi}{5} \\ \left[1 - \left(\frac{5\theta_1+2\pi}{2\pi}\right)^{\alpha} - \left(\frac{-5\theta_1}{2\pi}\right)^{\alpha}\right]\left(\frac{\pi-5\theta_1}{\pi}\right) + \\ \left[\left(\frac{5\theta_1+2\pi}{2\pi}\right)^{\alpha} + \left(\frac{-5\theta_1}{2\pi}\right)^{\alpha}\right]\left(\frac{5\theta_1+2\pi}{2\pi}\right), & \beta_1' - \frac{\pi}{5} \leq \beta < \beta_1' \\ \left[\left(\frac{5\theta_1}{\pi}\right)^{\alpha} + \left(\frac{\pi-5\theta_1}{\pi}\right)^{\alpha}\right]\left(\frac{\pi-5\theta_1}{\pi}\right), & \beta_1' \leq \beta < \beta_1' + \frac{\pi}{5} \end{cases}$$

where $\theta_1 = \beta - \beta_1' = \beta - 2.8\pi + \gamma$, $w_2(\gamma, \beta) =$ $$\begin{cases} \left[1 - \left(\frac{5\theta_2+3\pi}{2\pi}\right)^{\alpha} - \left(\frac{-5\theta_2-\pi}{2\pi}\right)^{\alpha}\right]\left(\frac{5\theta_2+\pi}{\pi}\right), & \beta_2' - \frac{2\pi}{5} \leq \beta < \beta_2' - \frac{\pi}{5} \\ \left[1 - \left(\frac{5\theta_2+\pi}{\pi}\right)^{\alpha} - \left(\frac{-5\theta_2}{\pi}\right)^{\alpha}\right]\left(\frac{\pi-5\theta_2}{\pi}\right) + \\ \left[\left(\frac{5\theta_2+\pi}{\pi}\right)^{\alpha} + \left(\frac{-5\theta_2}{\pi}\right)^{\alpha}\right]\left(\frac{5\theta_2+\pi}{\pi}\right), & \beta_2' - \frac{\pi}{5} \leq \beta < \beta_2' \\ \left[\left(\frac{5\theta_2}{\pi}\right)^{\alpha} + \left(\frac{\pi-5\theta_2}{\pi}\right)^{\alpha}\right]\left(\frac{\pi-5\theta_2}{\pi}\right), & \beta_2' \leq \beta < \beta_2' + \frac{\pi}{5} \\ \left[1 - \left(\frac{5\theta_2-\pi}{\pi}\right)^{\alpha} - \left(\frac{2\pi-5\theta_2}{\pi}\right)^{\alpha}\right]\left(\frac{\pi-5\theta_2}{\pi}\right), & \beta_2' + \frac{\pi}{5} \leq \beta < \beta_2' + \frac{2\pi}{5} \end{cases}$$

where $\theta_2 = \beta - \beta_2' = \beta - 2\pi + \gamma$, $w_3(\gamma, \beta) =$ $$\begin{cases} \left[1 - \left(\frac{5\theta_3+2\pi}{\pi}\right)^{\alpha} - \left(\frac{-5\theta_3-\pi}{\pi}\right)^{\alpha}\right]\left(\frac{5\theta_3+\pi}{\pi}\right) & \beta_3' - \frac{2\pi}{5} \leq \beta < \beta_3' - \frac{\pi}{5} \\ \left[1 - \left(\frac{5\theta_3+\pi}{\pi}\right)^{\alpha} - \left(\frac{-5\theta_3}{\pi}\right)^{\alpha}\right]\left(\frac{\pi-5\theta_3}{\pi}\right) + \\ \left[\left(\frac{5\theta_3+\pi}{\pi}\right)^{\alpha} + \left(\frac{-5\theta_3}{\pi}\right)^{\alpha}\right]\left(\frac{5\theta_3+\pi}{\pi}\right) & \beta_3' - \frac{\pi}{5} \leq \beta < \beta_3' \\ \left[1 - \left(\frac{5\theta_3}{\pi}\right)^{\alpha} - \left(\frac{\pi-5\theta_3}{\pi}\right)^{\alpha}\right]\left(\frac{\pi+5\theta_3}{\pi}\right) + \\ \left[\left(\frac{5\theta_3}{\pi}\right)^{\alpha} + \left(\frac{\pi-5\theta_3}{\pi}\right)^{\alpha}\right]\left(\frac{\pi-5\theta_3}{\pi}\right) & \beta_3' \leq \beta < \beta_3' + \frac{\pi}{5} \\ \left[1 - \left(\frac{5\theta_3-\pi}{2\pi}\right)^{\alpha} - \left(\frac{3\pi-5\theta_3}{2\pi}\right)^{\alpha}\right]\left(\frac{\pi-5\theta_3}{\pi}\right) & \beta_3' + \frac{\pi}{5} \leq \beta < \beta_3' + \frac{2\pi}{5} \end{cases}$$

where $\theta_3 = \beta - \beta_3' = \beta - 1.2\pi + \gamma$, and $w_4(\gamma, \beta) =$ $$\begin{cases} \left[1 - \left(\frac{5\theta_4+2\pi}{\pi}\right)^{\alpha} - \left(\frac{-5\theta_4-\pi}{\pi}\right)^{\alpha}\right]\left(\frac{5\theta_4+\pi}{\pi}\right) & \beta_4' - \frac{2\pi}{5} \leq \beta < \beta_4' - \frac{\pi}{5} \\ \left[\left(\frac{5\theta_4+\pi}{\pi}\right)^{\alpha} + \left(\frac{-5\theta_4}{\pi}\right)^{\alpha}\right]\left(\frac{\pi+5\theta_4}{\pi}\right) & \beta_4' - \frac{\pi}{5} \leq \beta < \beta_4' \\ \left[1 - \left(\frac{5\theta_4}{2\pi}\right)^{\alpha} - \left(\frac{2\pi-5\theta_4}{2\pi}\right)^{\alpha}\right]\left(\frac{\pi+5\theta_4}{\pi}\right) + \\ \left[\left(\frac{5\theta_4}{2\pi}\right)^{\alpha} + \left(\frac{2\pi-5\theta_4}{2\pi}\right)^{\alpha}\right]\left(\frac{2\pi-5\theta_4}{2\pi}\right) & \beta_4' \leq \beta < \beta_4' + \frac{\pi}{5} \\ \left[\left(\frac{5\theta_4}{2\pi}\right)^{\alpha} + \left(\frac{2\pi-5\theta_4}{2\pi}\right)^{\alpha}\right]\left(\frac{2\pi-5\theta_4}{2\pi}\right) & \beta_4' + \frac{\pi}{5} \leq \beta < \beta_4' + \frac{2\pi}{5} \end{cases}$$

where $\theta_4 = \beta - \beta_4' = \beta - 0.4\pi + \gamma$, $\beta_1'=2.8\pi-\gamma$, $\beta_2'=2\pi-\gamma$, $\beta_3'=1.2\pi-\gamma$, and $\beta_4'=0.4\pi-\gamma$;

$\beta_1'$, $\beta_2'$, $\beta_3'$, and $\beta_4'$ represent view angles intersecting the POR for detector rows R1, R2, R3, and R4, respectively, and $\gamma$ represents a detector angle.

26. A system in accordance with claim 16 further configured to apply a set of weights to the attenuation measurements prior to said filtering and backprojecting.

27. A system in accordance with claim 26 wherein said system being configured to apply a set of weights to the attenuation measurements comprises said system being configured to apply Lagrange weights to the attenuation measurements.

28. A system in accordance with claim 27 wherein said system being configured to apply Lagrange weights to the attenuation measurements comprises said system being configured to apply third order Lagrange weights to measurements from four detector rows.

29. A system in accordance with claim 16 having 4 detector rows, and said system being configured to helically scan the object to obtain attenuation measurements comprises said system being configured to helically scan the object at a pitch of 2.5:1, and to estimate at least one projection along the curved plane of reconstruction said system is further configured to estimate projections along the curved plane of reconstruction written as $\beta_1'=2.8\pi-\gamma$, $\beta_2'=2\pi-\gamma$, $\beta_3'=1.2\pi-\gamma$, and $\beta_4'=0.4\pi-\gamma$, where $\beta_1'$, $\beta_2'$, $\beta_3'$, and $\beta_4'$ represent view angles in a curved plane for corresponding detector rows R1, R2, R3, and R4, respectively, and $\gamma$ represents a detector angle.

30. A system in accordance with claim 16 further configured to apply interpolation and extrapolation to determine weights to be applied to the attenuation measurements.

* * * * *